United States Patent
Smith et al.

(10) Patent No.: US 12,186,558 B2
(45) Date of Patent: Jan. 7, 2025

(54) ELECTRO-ACOUSTIC INTERACTION CONTROL IN AUDITORY PROSTHESES

(71) Applicant: Cochlear Limited, Macquarie University (AU)

(72) Inventors: Zachary Mark Smith, Pymble (AU); Bastiaan Van Dijk, Antwerp (BE)

(73) Assignee: Cochlear Limited, Macquarie University (AU)

( * ) Notice: Subject to any disclaimer, the term of this patent is extended or adjusted under 35 U.S.C. 154(b) by 400 days.

(21) Appl. No.: 16/770,985

(22) PCT Filed: Dec. 7, 2018

(86) PCT No.: PCT/IB2018/059767
§ 371 (c)(1),
(2) Date: Jun. 9, 2020

(87) PCT Pub. No.: WO2019/116186
PCT Pub. Date: Jun. 20, 2019

(65) Prior Publication Data
US 2020/0330764 A1    Oct. 22, 2020

Related U.S. Application Data

(60) Provisional application No. 62/598,701, filed on Dec. 14, 2017.

(51) Int. Cl.
*A61N 1/36* (2006.01)
*H04R 25/00* (2006.01)

(52) U.S. Cl.
CPC ....... *A61N 1/36039* (2017.08); *H04R 25/606* (2013.01); *H04R 2225/67* (2013.01)

(58) Field of Classification Search
CPC .................... H04R 25/606; A61N 1/36039
See application file for complete search history.

(56) References Cited

U.S. PATENT DOCUMENTS 7,860,573 B2   12/2010   van den Honert
8,498,714 B2   7/2013   Litvak
8,761,894 B2   6/2014   Litvak
(Continued)

FOREIGN PATENT DOCUMENTS

KR   101499089 B1   3/2015

OTHER PUBLICATIONS

International Search Report and Written Opinion received in international application No. PCT/IB2018/059767, dated Apr. 15, 2019 (12 pages).

*Primary Examiner* — Rex R Holmes
*Assistant Examiner* — Jannifer L Ghand
(74) *Attorney, Agent, or Firm* — Edell, Shapiro & Finnan, LLC

(57) ABSTRACT

Presented herein are techniques to control the spread of current beyond, in an apical direction, a predetermined location/point in the cochlea. As a result, the techniques presented herein create a protected apical zone at an apical side of the predetermined location for undisturbed acoustic temporal coding (i.e., an apical region of the cochlea in which the voltage fields from delivered current signals are nulled, minimized, or otherwise controlled in order to eliminate, reduce, or otherwise limit electro-acoustic interactions that could negatively affect remaining low-frequency hair cells).

36 Claims, 14 Drawing Sheets

(56) References Cited

U.S. PATENT DOCUMENTS

| | | |
|---|---|---|
| 8,954,158 B2 | 2/2015 | Smith |
| 9,031,661 B2 | 5/2015 | Smith |
| 9,050,467 B2 | 6/2015 | Litvak |
| 9,056,205 B2 | 6/2015 | Litvak |
| 2005/0261748 A1* | 11/2005 | van Dijk ............ A61N 1/36039 607/57 |
| 2006/0247735 A1* | 11/2006 | Honert .................. A61N 1/323 607/57 |
| 2006/0287690 A1* | 12/2006 | Bouchataoui ...... A61N 1/36039 607/57 |
| 2010/0280307 A1* | 11/2010 | Lineaweaver ..... A61N 1/36038 607/57 |
| 2011/0093038 A1* | 4/2011 | Honert ................ A61N 1/0541 607/57 |
| 2015/0251006 A1 | 9/2015 | Qazi |
| 2015/0258337 A1* | 9/2015 | Long ................. A61N 1/36038 607/57 |
| 2015/0341731 A1* | 11/2015 | Polak ................ A61N 1/0541 600/25 |
| 2016/0279412 A1* | 9/2016 | Polak ................ A61N 1/36038 |
| 2017/0080226 A1 | 3/2017 | Akhoun |
| 2017/0165487 A1 | 6/2017 | van den Honert |
| 2017/0340876 A1* | 11/2017 | Vanpoucke ........ A61N 1/36038 |

* cited by examiner

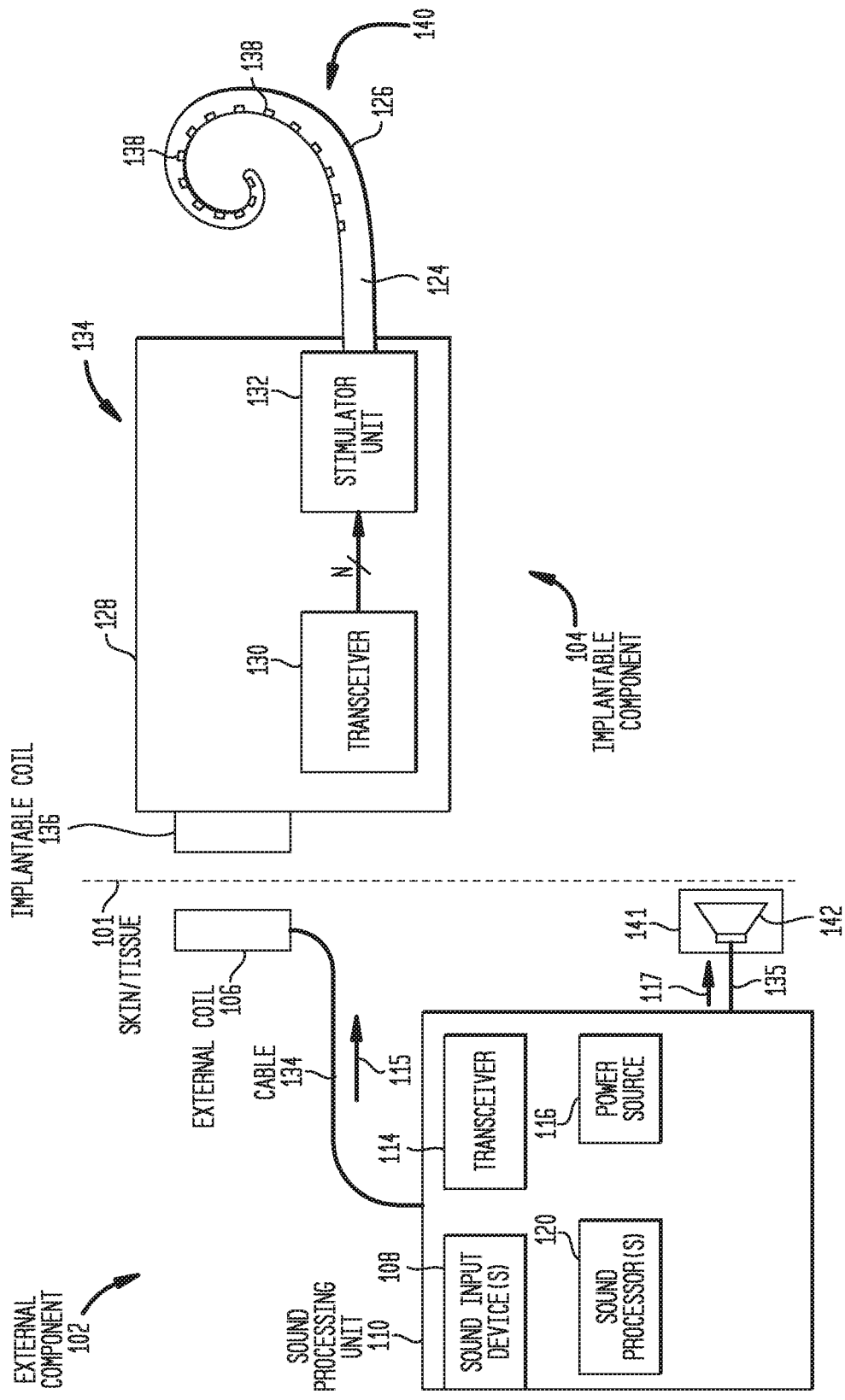

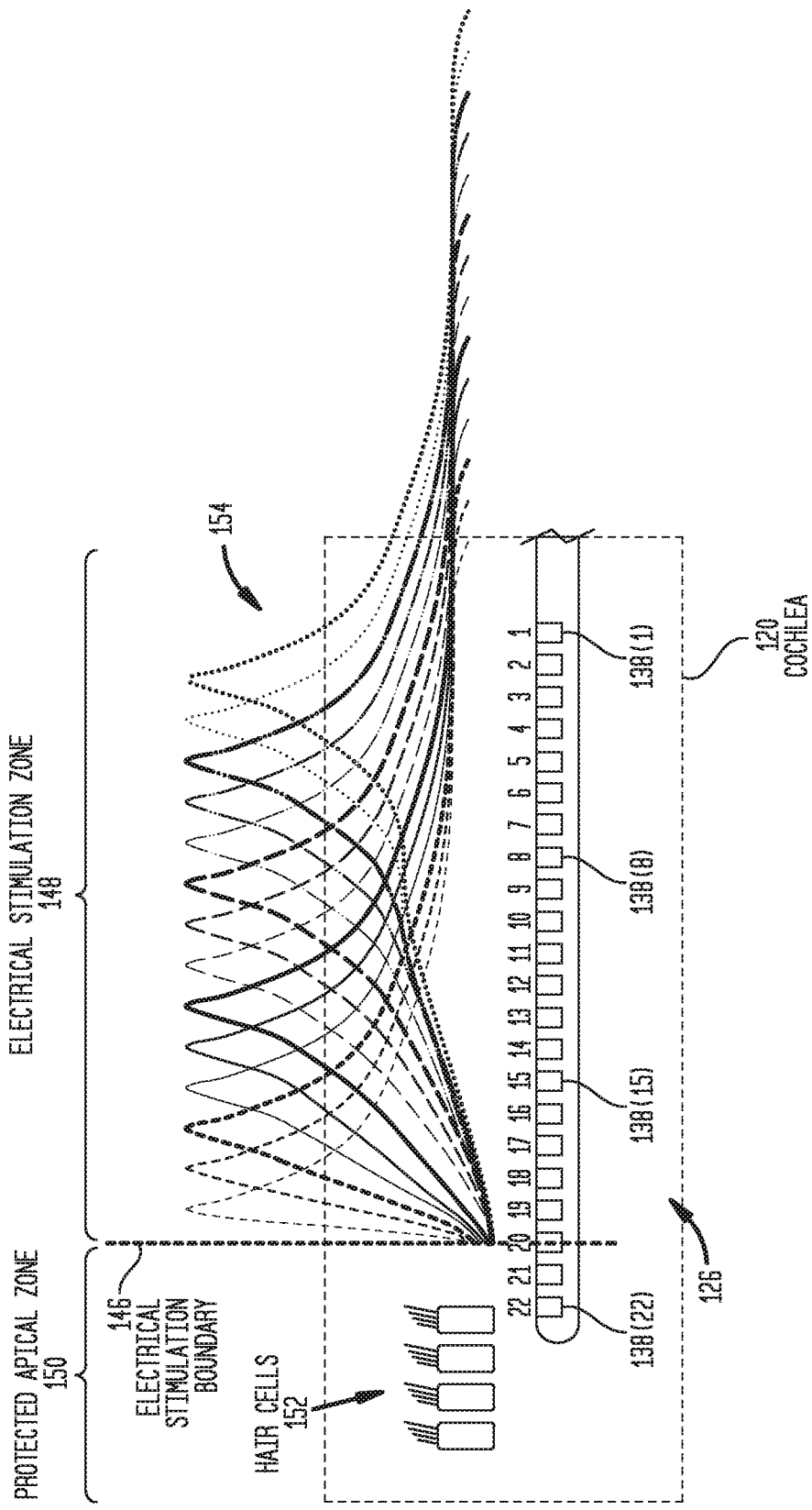

FIG. 6A

| ELECTRODE | 1 | 2 | 3 | 4 | 5 | 6 | 7 | 8 | 9 | 10 | 11 | 12 | 13 | 14 | 15 | 16 | 17 | 18 | 19 | 20 | 21 | 22 |
|---|---|---|---|---|---|---|---|---|---|---|---|---|---|---|---|---|---|---|---|---|---|---|
| VOLTAGE [mV] | 75 | 79 | 84 | 89 | 95 | 100 | 104 | 109 | 116 | 123 | 131 | 141 | 149 | 164 | 178 | 213 | 310 | 211 | 186 | 174 | 169 | 165 |

FIG. 6B

| ELECTRODE | 1 | 2 | 3 | 4 | 5 | 6 | 7 | 8 | 9 | 10 | 11 | 12 | 13 | 14 | 15 | 16 | 17 | 18 | 19 | 20 | 21 | 22 |
|---|---|---|---|---|---|---|---|---|---|---|---|---|---|---|---|---|---|---|---|---|---|---|
| VOLTAGE [mV] | 75 | 79 | 84 | 89 | 95 | 100 | 104 | 109 | 116 | 123 | 131 | 141 | 149 | 164 | 178 | 213 | 310 | 106 | 0 | 0 | 0 | 0 |

FIG. 7D

| ELECTRODE | 22 | 21 | 20 | 19 | 18 | 17 | 16 | 15 | 14 | 13 | 12 | 11 | 10 | 9 | 8 | 7 | 6 | 5 | 4 | 3 | 2 | 1 |
|---|---|---|---|---|---|---|---|---|---|---|---|---|---|---|---|---|---|---|---|---|---|---|
| CURRENT (uA) | -55 | -44 | -62 | -101 | -20 | 292 | 31 | 21 | 17 | 13 | 10 | 8 | 5 | 7 | 5 | 4 | 4 | 4 | 3 | 3 | 4 | 6 |

FIG. 8A

| ELECTRODE | 22 | 21 | 20 | 19 | 18 | 17 | 16 | 15 | 14 | 13 | 12 | 11 | 10 | 9 | 8 | 7 | 6 | 5 | 4 | 3 | 2 | 1 |
|---|---|---|---|---|---|---|---|---|---|---|---|---|---|---|---|---|---|---|---|---|---|---|
| VOLTAGE [mV] | 116 | 117 | 118 | 117 | 119 | 123 | 128 | 133 | 139 | 150 | 168 | 229 | 364 | 213 | 169 | 151 | 138 | 127 | 117 | 108 | 102 | 95 |

FIG. 8B

| ELECTRODE | 22 | 21 | 20 | 19 | 18 | 17 | 16 | 15 | 14 | 13 | 12 | 11 | 10 | 9 | 8 | 7 | 6 | 5 | 4 | 3 | 2 | 1 |
|---|---|---|---|---|---|---|---|---|---|---|---|---|---|---|---|---|---|---|---|---|---|---|
| VOLTAGE [mV] | 0 | 0 | 0 | 0 | 13 | 27 | 43 | 59 | 77 | 100 | 131 | 204 | 364 | 213 | 169 | 151 | 138 | 127 | 117 | 108 | 102 | 95 |

FIG. 9D

| ELECTRODE | 22 | 21 | 20 | 19 | 18 | 17 | 16 | 15 | 14 | 13 | 12 | 11 | 10 | 9 | 8 | 7 | 6 | 5 | 4 | 3 | 2 | 1 |
|---|---|---|---|---|---|---|---|---|---|---|---|---|---|---|---|---|---|---|---|---|---|---|
| CURRENT (uA) | -26 | -19 | -23 | -25 | -14 | -17 | -12 | -6 | -1 | -2 | 5 | -2 | 221 | 13 | 10 | 7 | 7 | 7 | 6 | 4 | 4 | 7 |

┌─────────────────────────────────────────┐
│ OBTAINING SOUNDS AT AN AUDITORY PROSTHESIS │ ─ 182
│ COMPRISING A STIMULATING ASSEMBLY IMPLANTED │
│ IN A COCHLEA OF A RECIPIENT, WHEREIN THE │
│ STIMULATING ASSEMBLY COMPRISES A PLURALITY │
│ OF LONGITUDINALLY SPACED ELECTRODES │
└─────────────────────────────────────────┘
                    ↓
┌─────────────────────────────────────────┐
│ CONVERTING THE SOUNDS INTO A FIRST SET │ ─ 184
│ OF CURRENT SIGNALS FOR DELIVERY TO THE │
│ COCHLEA OF THE RECIPIENT │
└─────────────────────────────────────────┘
                    ↓
┌─────────────────────────────────────────┐
│ DELIVERING THE CURRENT SIGNALS TO THE COCHLEA │ ─ 186
│ VIA A FIRST SET OF ELECTRODES, WHEREIN THE │
│ CURRENT SIGNALS ARE ASYMMETRICALLY CURRENT WEIGHTED │
│ TO EVOKE PERCEPTION OF ONE OR MORE FREQUENCIES │
│ OF THE SOUND SIGNALS AND TO SUBSTANTIALLY NULL, │
│ AT LOCATIONS APICAL TO A PREDETERMINED LOCATION IN │
│ THE COCHLEA, A VOLTAGE FIELD RESULTING FROM │
│ DELIVERY OF THE FIRST SET OF CURRENT │
│ SIGNALS TO THE COCHLEA │
└─────────────────────────────────────────┘

ELECTRO-ACOUSTIC INTERACTION CONTROL IN AUDITORY PROSTHESES

BACKGROUND

Field of the Invention

Aspects presented herein relate generally to techniques for controlling electro-acoustic interactions in auditory prostheses.

Related Art

Hearing loss, which may be due to many different causes, is generally of two types, conductive and/or sensorineural. Conductive hearing loss occurs when the normal mechanical pathways of the outer and/or middle ear are impeded, for example, by damage to the ossicular chain or ear canal. Sensorineural hearing loss occurs when there is damage to the inner ear, or to the nerve pathways from the inner ear to the brain.

Individuals who suffer from conductive hearing loss typically have some form of residual hearing because the hair cells in the cochlea are undamaged. As such, individuals suffering from conductive hearing loss typically receive an auditory prosthesis that generates motion of the cochlea fluid. Such auditory prostheses include, for example, acoustic hearing aids, bone conduction devices, and direct acoustic stimulators.

In many people who are profoundly deaf, however, the reason for their deafness is sensorineural hearing loss. Those suffering from some forms of sensorineural hearing loss are unable to derive suitable benefit from auditory prostheses that generate a pressure wave in the cochlear fluid. Such individuals can benefit from implantable auditory prostheses that stimulate nerve cells of the recipient's auditory system in other ways (e.g., electrical, optical and the like). Cochlear implants are often proposed when the sensorineural hearing loss is due to the absence or destruction of the cochlear hair cells, which transduce acoustic signals into nerve impulses. An auditory brainstem stimulator is another type of stimulating auditory prosthesis that might also be proposed when a recipient experiences sensorineural hearing loss due to damage to the auditory nerve.

Certain individuals suffer from only partial sensorineural hearing loss and, as such, retain at least some residual hearing. These individuals may be candidates for electro-acoustic hearing prostheses.

SUMMARY

In one aspect, a method is provided. The method comprises: determining an electrical stimulation boundary within a cochlea of a recipient of an auditory prosthesis comprising an intra-cochlear stimulating assembly, wherein the stimulating assembly comprises a plurality of longitudinally spaced electrodes forming a plurality of multipolar stimulation channels; and determining current weights for at least one of the plurality of stimulation channels at a basal side of the electrical stimulation boundary, wherein the current weights are configured to for use in generating current signals for delivery to the cochlea via the at least one stimulation channel to evoke perception of one or more frequencies of a sound obtained at the auditory prosthesis while creating a protected apical zone at an apical side of the electrical stimulation boundary.

In another aspect, a method is provided. The method comprises: obtaining sounds at an auditory prosthesis comprising a stimulating assembly implanted in a cochlea of a recipient, wherein the stimulating assembly comprises a plurality of longitudinally spaced electrodes; converting the sounds into a first set of current signals for delivery to the cochlea of the recipient; and delivering the current signals to the cochlea via a first set of electrodes, wherein the current signals are asymmetrically weighted to evoke perception of one or more frequencies of the sound signals and to substantially null, at locations apical to a predetermined location in the cochlea, a voltage field resulting from delivery of the first set of current signals to the cochlea.

In another aspect, a method is provided. The method comprises: determining an electrical stimulation boundary within a cochlea of a recipient of an auditory prosthesis comprising an intra-cochlear stimulating assembly, wherein the stimulating assembly comprises a plurality of longitudinally spaced electrodes forming a plurality of multipolar stimulation channels; and determining asymmetric current weights for at least one of the plurality of stimulation channels at a basal side of the electrical stimulation boundary, wherein the asymmetric current weights are configured to for use in generating current signals for delivery to the cochlea via the at least one stimulation channel to evoke perception of one or more frequencies of a sound obtained at the auditory prosthesis and to control the spread of current beyond, in an apical direction, the electrical stimulation boundary in the cochlea.

In another aspect, one or more non-transitory computer readable storage media encoded with instructions are provided. The instructions, when executed by a processor, cause the processor to: determine a predetermined location within a cochlea of a recipient of an auditory prosthesis comprising an intra-cochlear stimulating assembly, wherein the stimulating assembly comprises a plurality of longitudinally spaced electrodes; and determine asymmetric current weights for a first set of the electrodes, wherein the asymmetric current weights are configured to for use in generating current signals for delivery to the cochlea via the first set of electrodes to evoke perception of one or more frequencies of a sound obtained at the auditory prosthesis and to substantially null, at locations apical to a predetermined location in the cochlea, a voltage field resulting from delivery of the first set of current signals to the cochlea.

BRIEF DESCRIPTION OF THE DRAWINGS

Embodiments of the present invention are described herein in conjunction with the accompanying drawings, in which:

FIG. 1B is a block diagram of the electro-acoustic hearing prosthesis of FIG. 1A;

FIG. 2 is a schematic diagram of a stimulating assembly positioned in a recipient's cochlea, in accordance with certain embodiments presented herein;

FIG. 6A is a table illustrating expected voltages across a stimulating assembly positioned in a cochlea of a recipient for a first stimulation channel, in accordance with certain embodiments presented herein:

FIG. 6B is a table illustrating target apical protection voltages across a stimulating assembly positioned in a cochlea of a recipient to create a protected apical zone for a first stimulation channel, in accordance with certain embodiments presented herein;

FIG. 7D is a table listing the current values shown in FIG. 7C:

FIG. 8A is a table illustrating expected voltages across a stimulating assembly positioned in a cochlea of a recipient for a first stimulation channel, in accordance with certain embodiments presented herein;

FIG. 8B is a table illustrating target apical protection voltages across a stimulating assembly positioned in a cochlea of a recipient to create a protected apical zone for a first stimulation channel, in accordance with certain embodiments presented herein;

FIG. 9D is a table listing the current values shown in FIG. 7C:

FIG. 11 is a flowchart of a method, in accordance with embodiments presented herein.

DETAILED DESCRIPTION

Figure 1A:
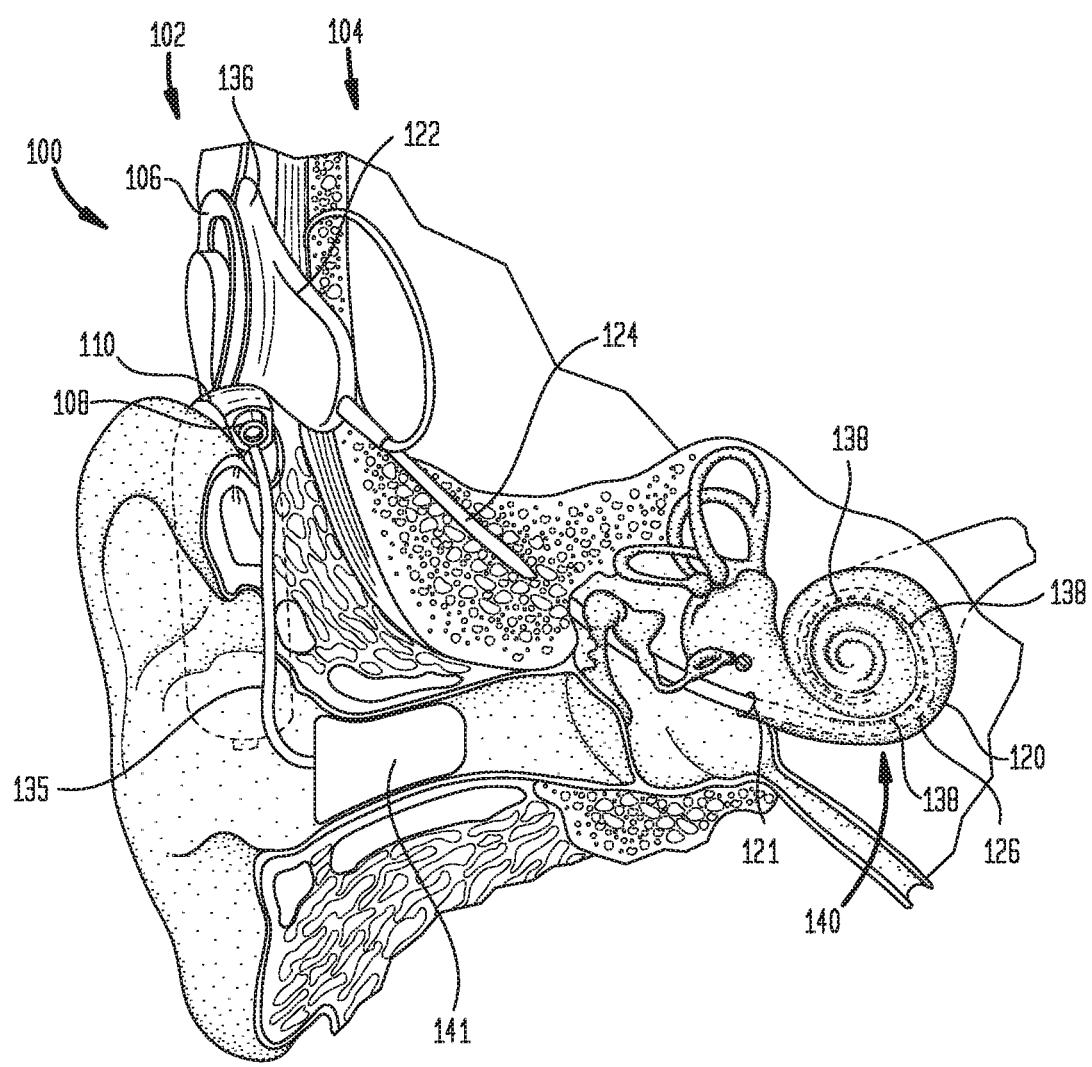
FIG. 1A is a schematic diagram illustrating an electro-acoustic hearing prosthesis, in accordance with certain embodiments presented herein.

Individuals suffer from different types of hearing loss (e.g., conductive and/or sensorineural) and/or different degrees/severity of hearing loss. However, it is now common for many auditory prosthesis recipients to retain some residual natural hearing ability (residual hearing) after receiving the auditory prosthesis. For example, progressive improvements in the design of intra-cochlear electrode arrays (stimulating assemblies), surgical implantation techniques, tooling, etc. have enabled atraumatic surgeries which preserve at least some of the recipient's fine inner ear structures (e.g., cochlea hair cells) and the natural cochlea function, particularly in the lower frequency regions of the cochlea.

Due, at least in part, to the ability to preserve residual hearing, the number of recipients who are candidates for different types of implantable auditory prostheses, such as electro-acoustic hearing prostheses, cochlear implants, tinnitus stimulators, etc. has continued to expand. As such, it is becoming increasingly common for auditory prosthesis recipients to rely on both electrical stimulation (i.e., current signals) and acoustic stimulation (i.e., natural or amplified acoustic sounds) at the same ear. Typically, due to the limits of residual hearing, the acoustic stimulation is used to present sound signal components corresponding to the lower frequencies of sound signals, while the electrical stimulation is used to present sound signal components corresponding to the higher frequencies of sound signals.

Recipients with residual hearing typically benefit from having the acoustic stimulation in addition to the electrical stimulation, because the acoustic stimulation adds a more "natural" sound to their hearing perception over the electrical stimulation signals only in that ear. In particular, temporal coding of auditory signals is particularly important for low frequencies and is best achieved with acoustic stimulation. As such, combined electric-acoustic stimulation benefits specifically from this low-frequency acoustic coding. For example, the addition of the acoustic stimulation can provide improved pitch and music perception and/or appreciation, as the acoustic signals may contain a more salient lower frequency (e.g., fundamental pitch, F0) representation than is possible with electrical stimulation. Other benefits of residual hearing may include, for example, improved sound localization, binaural release from unmasking, the ability to distinguish acoustic signals in a noisy environment, etc.

The cochlea is tonotopically mapped, meaning that certain regions/areas of the cochlea respond to different frequencies of sound. In general, the areas that respond to lower frequencies are located towards the apical/distal end of the cochlea, while the areas that respond to higher frequencies are located towards the basal/proximal end of the cochlea. Typically, a recipient's residual hearing remains in the lower frequency areas (i.e., the more apical areas of the cochlea) and these are the areas that can be stimulated using acoustic stimulation. In contrast, the higher frequency areas (i.e., the more basal areas of the cochlea) typically do not include residual hearing and these are the areas that are stimulated using acoustic stimulation.

Despite the benefits of acoustic stimulation, the present applicant has discovered that conventional stimulation techniques are negatively affected by electro-acoustic interactions within the cochlea. That is, the present applicant has discovered that there is a risk that delivery of electric stimulation (current signals) in the higher frequency regions of the cochlea can interfere with acoustic stimulation in the lower frequency areas of the cochlea. As such, presented herein are techniques to limit, restrict, or otherwise control the encroachment/intrusion of the electric stimulation into the apical regions of the cochlea that rely on acoustic stimulation (e.g., prevent spread of the current from mid-frequency and high-frequency areas to low-frequency areas).

More specifically, the techniques presented herein use asymmetric current focusing (asymmetric multipolar channel configurations) to control the spread of current beyond/past, in an apical direction, a predetermined location/point in the cochlea, sometimes referred to herein as the "electrical stimulation boundary." The multipolar channel configurations are "asymmetric" in that the current weights for a stimulation channel are non-symmetrical and are specifically configured to limit the occurrence of voltages beyond the electrical stimulation boundary in the cochlea. As a result, the techniques presented herein create a so-called "protected acoustic zone" or "protected apical zone" at an apical side of the electrical stimulation boundary for undisturbed acoustic temporal coding (i.e., an apical region of the cochlea in which the voltage fields from delivered current signals are nulled, minimized, or otherwise controlled in order to eliminate, reduce, or otherwise limit electro-acoustic interactions that could negatively affect remaining low-frequency hair cells). That is, as used herein, a "protected acoustic zone" or "protected apical zone" refers to an apically-located region of the cochlea that, when current signals are delivered to the more basally-located regions of the cochlea, will be exposed to average voltage fields that are below a predetermined threshold.

The techniques presented herein may be used with a number of different types of auditory prostheses that deliver electrical stimulation (current signals) alone or in combination with acoustic stimulation, such as cochlear implants, auditory brainstem stimulators, tinnitus stimulators, bi-modal hearing prostheses, electro-acoustic hearing prostheses, etc. Therefore, as used herein, "acoustic stimulation" may refer to the delivery of aided/amplified acoustic signals to the cochlea or to the delivery of unaided (natural) acoustic signals to the cochlea (i.e., reliance on natural hearing in the outer and middle ears).

Merely for ease of illustration, embodiments are primarily described herein with reference to one specific type of implantable auditory prostheses, namely an electro-acoustic hearing prosthesis comprising a cochlear implant portion and a hearing aid portion. Again, the techniques presented herein may be used with other types of hearing prostheses, including cochlear implants, electro-acoustic hearing prosthesis comprising other types of output devices (e.g., auditory brainstem stimulators, direct acoustic stimulators, bone conduction devices, etc.), etc.

FIG. 1A is schematic diagram of an exemplary electro-acoustic hearing prosthesis 100 configured to implement embodiments of the present invention, while FIG. 1B is a block diagram of the electro-acoustic hearing prosthesis. For ease of illustration, FIGS. 1A and 1B will be described together.

The electro-acoustic hearing prosthesis 100 includes an external component 102 and an internal/implantable component 104. The external component 102 is directly or indirectly attached to the body of the recipient and comprises a sound processing unit 110, an external coil 106, and, generally, a magnet (not shown in FIG. 1A) fixed relative to the external coil 106. The external coil 106 is connected to the sound processing unit 110 via a cable 134. The sound processing unit 110 comprises one or more sound input devices 108 (e.g., microphones, audio input ports, cable ports, telecoils, a wireless transceiver, etc.), a sound processor 112, an external transceiver unit (transceiver) 114, and power source 116. In the example of FIGS. 1A and 1B, the sound processing unit 110 is a behind-the-ear (BTE) sound processing unit. However, in other embodiments, the sound processing unit 110 could be a body-worn sound processing unit, a button sound processing unit, an in-the-ear (ITE) unit, etc.

Connected to the sound processing unit 110 (e.g., via a cable 135) is a hearing aid component 141. The hearing aid component 141 includes a receiver 142 (FIG. 1B) that may be, for example, positioned in or near the recipient's outer ear. The receiver 142 is an acoustic transducer that is configured to deliver acoustic signals (acoustic stimulation) to the recipient via the recipient's ear canal and middle ear.

FIGS. 1A and 1B illustrate the use of a receiver 142 to deliver acoustic stimulation to the recipient. However, as noted above, it is to be appreciated that the acoustic stimulation may be delivered in a number of other manners. For example, other embodiments may include an external or implanted vibrator that is configured to deliver acoustic stimulation to the recipient. In still other embodiments, the hearing aid component 141 could be omitted and the recipient's cochlea is acoustically stimulated using unaided acoustic signals provided to the recipient's cochlea via the natural hearing path (i.e., via the functioning outer ear and middle ear).

As shown in FIG. 1B, the implantable component 104 comprises an implant body (main module) 122, a lead region 124, and an elongate intra-cochlear stimulating assembly 126. The implant body 122 generally comprises a hermetically-sealed housing 128 in which an internal transceiver unit (transceiver) 130 and a stimulator unit 132 are disposed. The implant body 122 also includes an internal/implantable coil 136 that is generally external to the housing 128, but which is connected to the transceiver 130 via a hermetic feedthrough (not shown in FIG. 1B). Implantable coil 136 is typically a wire antenna coil comprised of multiple turns of electrically insulated single-strand or multi-strand platinum or gold wire. The electrical insulation of implantable coil 136 is provided by a flexible molding (e.g., silicone molding), which is not shown in FIG. 1B. Generally, a magnet is fixed relative to the implantable coil 136.

Elongate stimulating assembly 126 is configured to be at least partially implanted in the recipient's cochlea 120 and includes a plurality of longitudinally spaced intra-cochlear electrical stimulating contacts (electrodes) 138 that collectively form a contact array 140 for delivery of electrical stimulation (current signals) to the recipient's cochlea. In certain arrangements, the contact array 140 may include other types of stimulating contacts, such as optical stimulating contacts, in addition to the electrodes 138.

Stimulating assembly 126 extends through an opening 121 in the cochlea (e.g., cochleostomy, the round window, etc.) and has a proximal end connected to stimulator unit 132 via lead region 124 and a hermetic feedthrough (not shown in FIG. 1B). Lead region 124 includes a plurality of conductors (wires) that electrically couple the electrodes 138 to the stimulator unit 132.

Returning to external component 102, the sound input device(s) 108 are configured to detect/receive sound signals and to generate electrical output signals therefrom. The sound processor 112 is configured to execute sound processing that converts the output signals received from the sound input device(s) into coded data signals that represent acoustical and/or electrical stimulation for delivery to the recipient. That is, as noted, the electro-acoustic hearing prosthesis 100 operates to evoke perception by the recipient of sound signals received by the sound input device(s) 108 through the delivery of one or both of electrical stimulation signals and acoustic stimulation signals to the recipient. As such, depending on the current operational settings (operational "map"), the sound processor 112 is configured to convert the output signals received from the sound input device(s) into a first set of output signals representative of electrical stimulation and/or into a second set of output signals representative of acoustic stimulation. The output signals representative of electrical stimulation are represented in FIG. 1B by arrow 115, while the output signals representative of acoustic stimulation are represented in FIG. 1B by arrow 117.

The output signals 115 are provided to the transceiver 114. The transceiver 114 is configured to transcutaneously transfer the output signals 115, in an encoded manner, to the implantable component 104 via external coil 106. More specifically, the magnets fixed relative to the external coil 106 and the implantable coil 136 facilitate the operational alignment of the external coil 106 with the implantable coil 136. This operational alignment of the coils enables the external coil 106 to transmit the coded output signals 115, as well as power signals received from power source 116, to the implantable coil 136. In certain examples, external coil 106 transmits the encoded output signals 115 to implantable coil 136 via a radio frequency (RF) link. However, various other types of energy transfer, such as infrared (IR), electromagnetic, capacitive and inductive transfer, may be used to transfer the power and/or data from an external component to an electro-acoustic hearing prosthesis and, as such, FIG. 1B illustrates only one example arrangement.

In general, the encoded output signals 115 are received at the transceiver 130 and provided to the stimulator unit 132. The stimulator unit 132 is configured to utilize the output signals 115 to generate electrical stimulation (e.g., current signals) for delivery to the recipient's cochlea via one or more stimulating contacts 138. In this way, electro-acoustic hearing prosthesis 100 electrically stimulates the recipient's auditory nerve cells, bypassing absent or defective hair cells that normally transduce acoustic vibrations into neural activity, in a manner that causes the recipient to perceive one or more components of the received sound signals.

FIGS. 1A and 1B illustrate an arrangement in which the cochlear implant 100 includes an external component 102. However, it is to be appreciated that embodiments of the present invention may be implemented in auditory prostheses having alternative arrangements. For example, embodiments of the present invention may be implemented in a totally implantable auditory prosthesis. A totally implantable auditory prosthesis is an auditory prosthesis in which all components are configured to be implanted under skin/tissue of a recipient. Because all components are implantable, a totally implantable auditory prosthesis is configured to operate, for at least a finite period of time, without the need of an external device. However, an external device can be used to, for example, charge an internal power source (battery) of a totally implantable auditory prosthesis.

As noted above, it is common for auditory prosthesis recipients to retain at least part of their normal hearing functionality (i.e., retain at least some residual hearing). Therefore, the cochlea of an auditory prosthesis recipient can be acoustically stimulated upon delivery of an aided (or potentially unaided) acoustic signal to the recipient's outer ear. In the example of FIGS. 1A and 1B, the receiver 142 is used to aid the recipient's residual hearing. More specifically, the output signals 117 (i.e., the signals representative of acoustic stimulation) are provided to the receiver 142. The receiver 142 is configured to utilize the output signals 117 to generate the acoustic stimulation signals that are provided to the recipient. In other words, the receiver 142 is used to enhance, and/or amplify a sound signal which is delivered to the cochlea via the middle ear bones and oval window, thereby creating a pressure wave in the perilymph within the cochlea.

As such, the electro-acoustic hearing prosthesis 100 of FIGS. 1A and 1B is configured to deliver both acoustic stimulation and electrical stimulation (current signals) to a recipient. Acoustic stimulation combined with electrical stimulation is sometimes referred to herein as electro-acoustic stimulation. The electrical stimulation is generated from at least a first portion/segment (i.e., frequencies or frequency ranges) of the sound signals, while the acoustic stimulation signals are generated from at least a second portion of the sound signals. The recipient's operational settings, which are determined and set during a fitting process, dictate how the electro-acoustic hearing prosthesis 100 operates to convert sound signals into the acoustic and/or electrical stimulation.

As noted above, the present applicant has discovered that one problem arising from the use of electro-acoustic stimulation, or simply electrical stimulation in the presence of residual hearing, is the occurrence of electric-acoustic interactions within the cochlea. That is, in conventional electrical stimulation techniques, the electrical stimulation is allowed to spread, in an uncontrolled manner, into the apical regions of the cochlea that have residual hearing capabilities and that utilize acoustic stimulation to evoke a hearing percept. This spread of the electrical stimulation results in electric-acoustic interactions that may, for example, have a negative effect on the acoustic stimulation in the apical region (e.g., interfere with the acoustic coding of low-frequency temporal fine structure cues), damage existing inner ear hair cells, etc.

As such, presented herein are techniques that use asymmetric current focusing (asymmetric multipolar channel configurations) to create an electrical stimulation boundary within the cochlea. As described further below, in accordance with the techniques presented herein, the current signals (electrical stimulation) are delivered only on the basal side of the electrical stimulation boundary within the cochlea. The current signals are delivered (i.e., weighted) in a manner that results in the voltage fields from the delivered current signals being controlled (e.g., substantially nulled/minimized) in order to limit (e.g., substantially eliminate) electro-acoustic interactions on the apical side of the electrical stimulation boundary. As noted above, the result of the asymmetric current focusing is the creation of a protected apical zone at an apical side of the electrical stimulation boundary for undisturbed temporal coding (i.e., an apically-located region of the cochlea that, when current signals are delivered to the more basally-located regions of the cochlea, will be exposed to average voltage fields that are below a predetermined threshold).

Returning to the specific example of FIGS. 1A and 1B, as noted the electro-acoustic hearing prosthesis 100 is configured to convert the sound signals received at the sound input device(s) 108 into current signals that are to be delivered to the cochlea 120 to evoke perception of at least a portion of the sound signals. Due to the tonotopic mapping of the cochlea 120, different portions of the sound signals are delivered to different target locations/places of the cochlea 120 via different multipolar stimulation channels, sometimes referred to herein simply as stimulation channels. As used herein, a stimulation channel is a combination/set of the electrodes that are used simultaneously/collectively to deliver current signals to the cochlea 120 so as to elicit stimulation at a specific target location/place of the cochlea.

For ease of illustration, stimulation channels are generally defined herein with reference to a corresponding "central electrode" and one or more "secondary electrodes." The central electrode of a stimulation channel is the electrode closest to the peak in the voltage (e.g., the electrode closest to the specific target location/place of the cochlea). For example, reference to a stimulation channel "at electrode 10" refers to the stimulation channel having the tenth electrode from the basal end of the stimulating assembly as the corresponding central electrode; reference to a stimulation channel "at electrode 17" refers to stimulation channel having the seventeenth electrode as the corresponding central electrode; and so on. The secondary electrodes of a stimulation channel are one or more electrodes other than the central electrode that are used to control the resulting voltage fields.

Within a given stimulation channel, the current signals at different secondary electrodes may have different polarities (i.e., the current can be sourced at certain electrodes and sunk at other electrodes) and different relative magnitudes. The magnitudes of the current signals are generated in accordance with predetermined relative asymmetric current weights. Within a given stimulation channel, the current signals at the different electrodes have relative current weights so that the current signals evoke perception of a sound frequency portion at the target location of the cochlea. As described further below, in addition to being configured to evoke perception at the target location of the cochlea, the asymmetric current weights in accordance with embodiments of the present invention are also configured to control the spread of current beyond/past, in an apical direction, the electrical stimulation boundary in the cochlea (i.e., specifically configured to limit the occurrence of voltages beyond the electrical stimulation boundary in the cochlea). This results in the elimination or reduction of electro-acoustic interactions the apical side of a predetermined electrical-stimulation boundary that could negatively affect remaining low-frequency hair cells.

The process for determining the magnitudes of current signals for a stimulation, given a predetermined set of current weights for the channel, is sometimes referred to herein as channel encoding. In accordance with certain embodiments presented herein, the channel encoding process may be implemented by the sound processor 112 of the electro-acoustic hearing prosthesis 100. In other embodiments, the channel encoding process may be implemented by the stimulator unit 132.

FIG. 2 is a schematic diagram illustrating further details of stimulating assembly 126 of FIGS. 1A and 1B implanted in recipient's cochlea 120. In this example, the stimulating assembly 126 includes twenty-two (22) electrodes 138, labeled as electrodes 138(1)-138(22). Electrode 138(1) is the most basal electrode (i.e., the electrode located closest to the cochlea opening through which the stimulating assembly 126 is inserted), while electrode 138(22) is the most apical electrode (i.e., the electrode located closest to the cochlea apex).

FIG. 2 also illustrates an electrical stimulation boundary 146. As shown, the electrical stimulation boundary 146 generally divides the cochlea 120 into two regions or zones, referred to as the electrical stimulation zone 148 and the protected apical zone 150. For stimulation channels within the electrical stimulation zone 148 (i.e., stimulation channels having a central electrode on the basal side of the electrical stimulation boundary 146), trans-impedance matrix inversion techniques are used to minimize the apical spread of current beyond the electrical stimulation boundary 146. In general, the trans-impedance matrix inversion techniques create negative channel (current) weights at the stimulation channels within the electrical stimulation zone 148. The negative current weights are generally largest for the channels proximate to the electrical stimulation boundary 146 and decrease in magnitude (i.e., become less negative) as the channel center moves more basally. Stated differently, the current weights generally become less negative as the distance between the electrode(s) of the channel and the electrical stimulation boundary 146 increases (i.e., the current weights are a function of the distance between the electrode(s) of the channel and the electrical stimulation boundary 146).

The current weights created for the stimulation channels within the electrical stimulation zone 148 are set so as to limit the spread of current beyond/past, in an apical direction, the electrical stimulation boundary 146. However, the current weights created for the stimulation channels within the electrical stimulation zone 148 are also set so as to evoke perception of certain frequency/frequencies of received sound signals, such as the higher-frequency sound signals. Lower-frequency coding is provided by acoustic stimulation of the hair cells 152 located within the protected apical zone 150.

As noted, delivery of current signals via a stimulation channel create voltage fields within the cochlea. In accordance with embodiments presented herein, the channel encoding process includes asymmetric current focusing that sets the weights for the current signals such that, when the current is delivered to the cochlea, the protected apical zone 150 will be created (i.e., create an area in which the voltage fields from delivered current signals are nulled, minimized, or otherwise controlled in order to eliminate, reduce, or otherwise limit electro-acoustic interactions that could negatively affect remaining low-frequency hair cells). In FIG. 2, the lines 154 generally represent example voltage fields that could be created at each of electrodes 138(1)-138(19) to evoke perception of specific frequency/frequencies of received sound signals, while creating the protected apical zone 150 (i.e., limiting occurrence of voltages beyond the electrical stimulation boundary 146).

Figure 3:
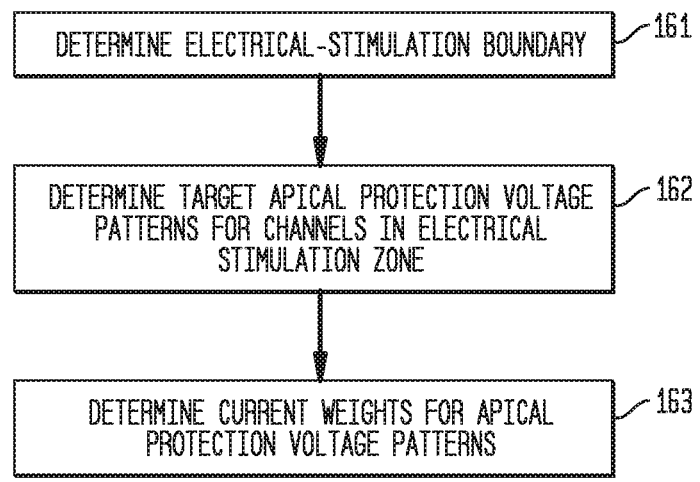
FIG. 3 is a flowchart of a method, in accordance with embodiments presented herein.

FIG. 3 is a flowchart illustrating one example method 160 for programming a device to perform techniques for creation of a protected apical zone upon delivery of current signals to a recipient, in accordance with embodiments presented herein. For ease of illustration, the method 160 of FIG. 3 will generally be described with reference to electro-acoustic hearing prosthesis 100 of FIGS. 1A, 1B, and 2.

Method 160 begins at 161 by determining the electrical stimulation boundary 146 for the recipient. The electrical stimulation boundary 146 is a location within the cochlea 120 beyond which, in the direction of low-frequency acoustic hearing (i.e., the apical direction), the voltage fields from current signals should be substantially nulled in order to limit electro-acoustic interactions that could negatively affect remaining low-frequency hair cells. The electrical stimulation boundary 146 may be set, for example, with reference to a location (e.g., a specific electrode) on the stimulating assembly 126.

In one embodiment, the electrical stimulation boundary 146 is set based on the recipient's audiogram, which can be measured or otherwise obtained (e.g., from clinical records). The recipient's audiogram, which is a graphical representation of the recipient's hearing capabilities, is used to determine which frequency ranges should be stimulated acoustically (i.e., which tonotopic regions of the cochlea have residual hearing). For example, the recipient's audiogram could be used to identify frequency areas of the cochlea having acoustic thresholds that are less than a predetermined threshold hearing level (e.g., less than 85 decibels Hearing Level (dB HL)). In certain embodiments, a cochlear-frequency map (e.g., a Greenwood map) is then used to determine location of the highest protected frequency (i.e., the upper end of the frequency range having acoustic thresholds that are below the predetermined threshold level). This location is referred to herein as the "location of highest protected frequency (HPF)." The electrical stimulation boundary 146 is then set at an electrode on the array that is located on the basal side of the location of the HPF. In one embodiment, the first electrode on the basal side of the location of the HPF is selected as the electrical stimulation boundary 146. In other embodiments, the electrical stimulation boundary 146 is placed even further toward the basal end of the cochlea 120 in order to create an additional buffer zone/region (i.e., the electrical stimulation boundary 146 is spaced from the location of HPF by one or more electrodes).

After setting the electrical stimulation boundary 146, at 162 target apical protection voltage field patterns are determined for the stimulation channels within the electrical stimulation zone 148 (i.e., for stimulation channels having a central electrode on the basal side of the electrical stimulation boundary 146). More specifically, in one embodiment, the recipient's trans-impedance matrix is first obtained (e.g., measured or obtained from clinical records). In one example, the recipient's trans-impedance matrix is measured by individually delivering current signals via each electrode of the stimulating assembly 126 at a known current level, i, and recording/measuring the resulting voltage, v, at all of the other electrodes. The trans-impedances, denoted as below in Equation 1, are calculated for each combination of stimulating electrode and recording electrode.

$$z_{i,j} = v_i / i_j,  \quad \text{Equation 1}$$

where $v_i$ is the voltage measured at a recording electrode and $i_j$ is the current delivered at the stimulating electrode.

The trans-impedances calculated for all pairs of electrodes are combined to form a full trans-impedance matrix (Z). For the 22-electrode stimulating assembly 126, the result is a 22×22 trans-impedance matrix.

In the embodiment of FIG. 3, at 162 after obtaining the trans-impedance matrix, expected voltage field patterns are determined for each stimulation channel within the electrical stimulation zone 148. The expected voltage field patterns are determined are based on the voltage-spread vectors, V, of monopolar channels sharing the same center electrode. The voltage spread vector for a monopolar channel using an electrode k, is denoted $V_k$.

The expected voltage field pattern is then converted to the target apical protection voltage field pattern by adjusting/setting the voltages for electrodes located at, and on the apical side of, the electrical stimulation boundary 146 to a value of zero. In certain embodiments, voltages at electrodes between the electrical stimulation boundary 146 and the center electrode of a given channel are also adjusted (e.g., gradually reduced) in order to avoid a sudden drop-off at the electrical stimulation boundary 146.

In accordance with embodiments presented herein, the target apical protection voltage field pattern for a center electrode, k, is referenced as $V'_k$. At 163 of method 160, the channel currents, $I'_k$, for each channel, k, that will create the target apical protection voltage pattern, $V'_k$, are determined using Equation 2, below, for all channels, k, on the basal side of the electrical stimulation boundary 148. According to Equation 2, below, the channel currents, $I'_k$, for each channel, k, are found by inverting the trans-impedance matrix, Z, and multiplying that with the target voltage field pattern $V'_k$. Finally, current weights, wk, can be defined for each channel, k, by dividing the currents of $I'_k$ by the current of the central electrode of the original monopolar channel, $I_k$. The resulting multipolar weights, w, can be stored for later usage when calculating how much current to deliver to the electrodes for a given location and desired intensity, according to the input sound (see Method 180).

$$I'_k = Z^{-1} V'_k \quad \text{Equation 2}$$

In summary, FIG. 3 illustrates a method for generation of relative asymmetric current weights for stimulation channels (asymmetric multipolar channel configurations) for reduced electric-acoustic interactions within the cochlea 120. Once generated, the relative asymmetric current weights for the stimulation channels are provided to, and stored in, the electro-acoustic hearing prosthesis 100 for generation of current signals (electrical stimulation), in real-time, for delivery to the recipient.

In certain embodiments, the operations of method 160 are performed at a computing device (e.g., computer, fitting system, etc.) that is configured to communicate with the electro-acoustic hearing prosthesis 100 (e.g., via a wired or wireless connection). As such, the electro-acoustic hearing prosthesis 100 is then programmed, by the computing device, to deliver acoustic stimulation, at appropriate gains, for the appropriate acoustic frequency ranges (i.e., tonotopic regions of the cochlea which have been determined at 161 to have sufficient residual hearing so as to be suitable for acoustic stimulation). The electro-acoustic hearing prosthesis 100 is also programmed, by the computing device, to deliver current signals at stimulation channels and with the current weights determined at 163 to represent the remaining frequencies.

To facilitate further understanding of the techniques presented herein, an illustrative example application of method 160 is described below with reference to FIGS. 4-9. In this example, the recipient is implanted with an intra-cochlear stimulating assembly that includes 22 electrodes. Prior to activation of the hearing prosthesis and the intra-cochlear stimulating assembly (i.e., before any stimulation has been delivered), the recipient is measured to have the audiogram 166 shown in FIG. 4.

The audiogram 166 illustrates that the recipient has significant levels of post-implantation residual hearing. As such, it is deemed appropriate to use acoustic amplification (i.e., a receiver) to acoustically stimulate the relatively lower frequency regions of the cochlea and to use electrical stimulation to stimulate the relatively higher frequency regions of the cochlea.

Figure 4:
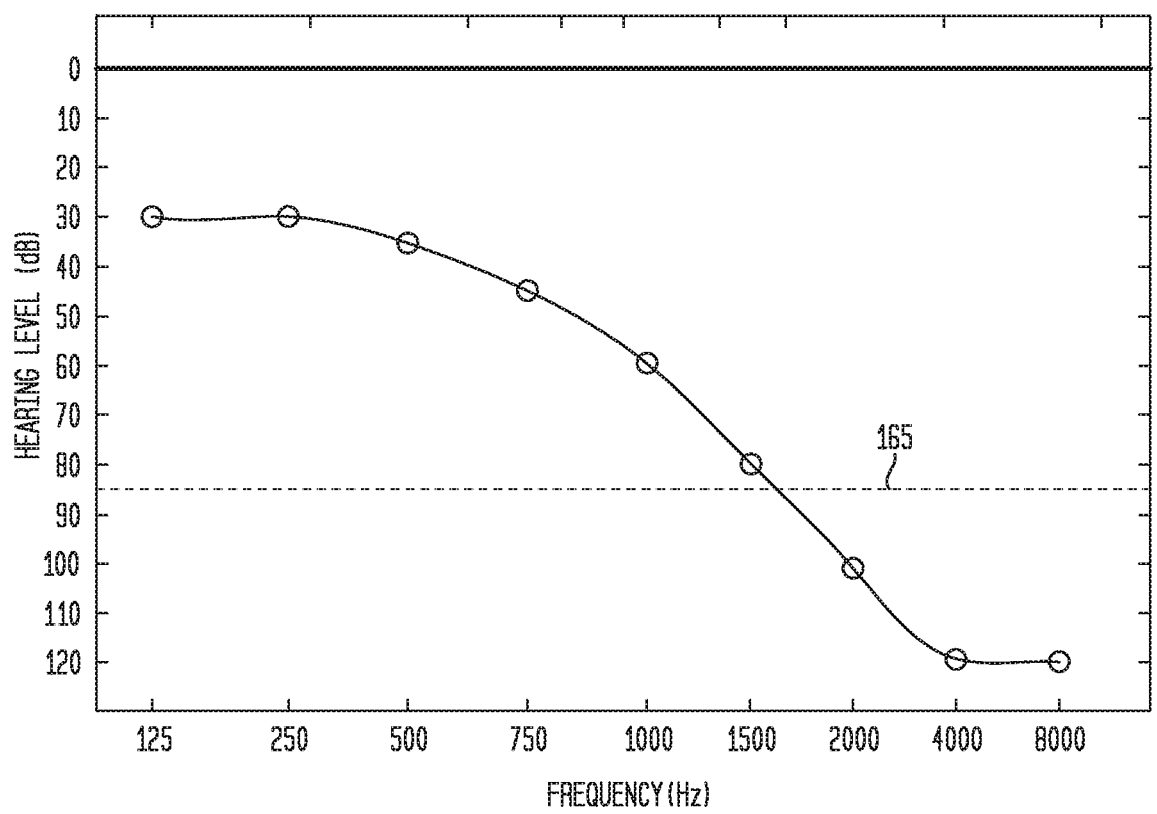
FIG. 4 is a diagram illustrating an example post-implantation audiogram of a recipient of an electro-acoustic hearing prosthesis, in accordance with certain embodiments presented herein.

In this example, an acoustic threshold of 85 dB HL (represented by the dashed line 165 in FIG. 4) is used to set the electrical-stimulation boundary for the recipient. As shown in FIG. 4, using the acoustic threshold of 85 dB HL results in acoustic frequencies of 1500 Hertz (Hz) and below suitable for being stimulated acoustically and, as such, having residual hearing capabilities (i.e., hair cells) that should be protected from electric stimulation. Stated differently, it is determined that hair cells in the tonotopic frequency range generally less than approximately 1500 Hz should be protected from electrical stimulation.

Using a cochlear-frequency map, it is determined that 1500 Hz corresponds to an insertion depth of approximately 18 mm (i.e., a distance of approximately 18 mm from the basal end of the cochlea) or an angle of 370 degrees, from the base of the cochlea. As such, the location of the highest protected frequency (HPF) is set to a location of 370 degrees. Using, for example, radiological imaging or another method, the angular locations of the electrodes inserted into the recipient's cochlea are determined.

Figure 5:
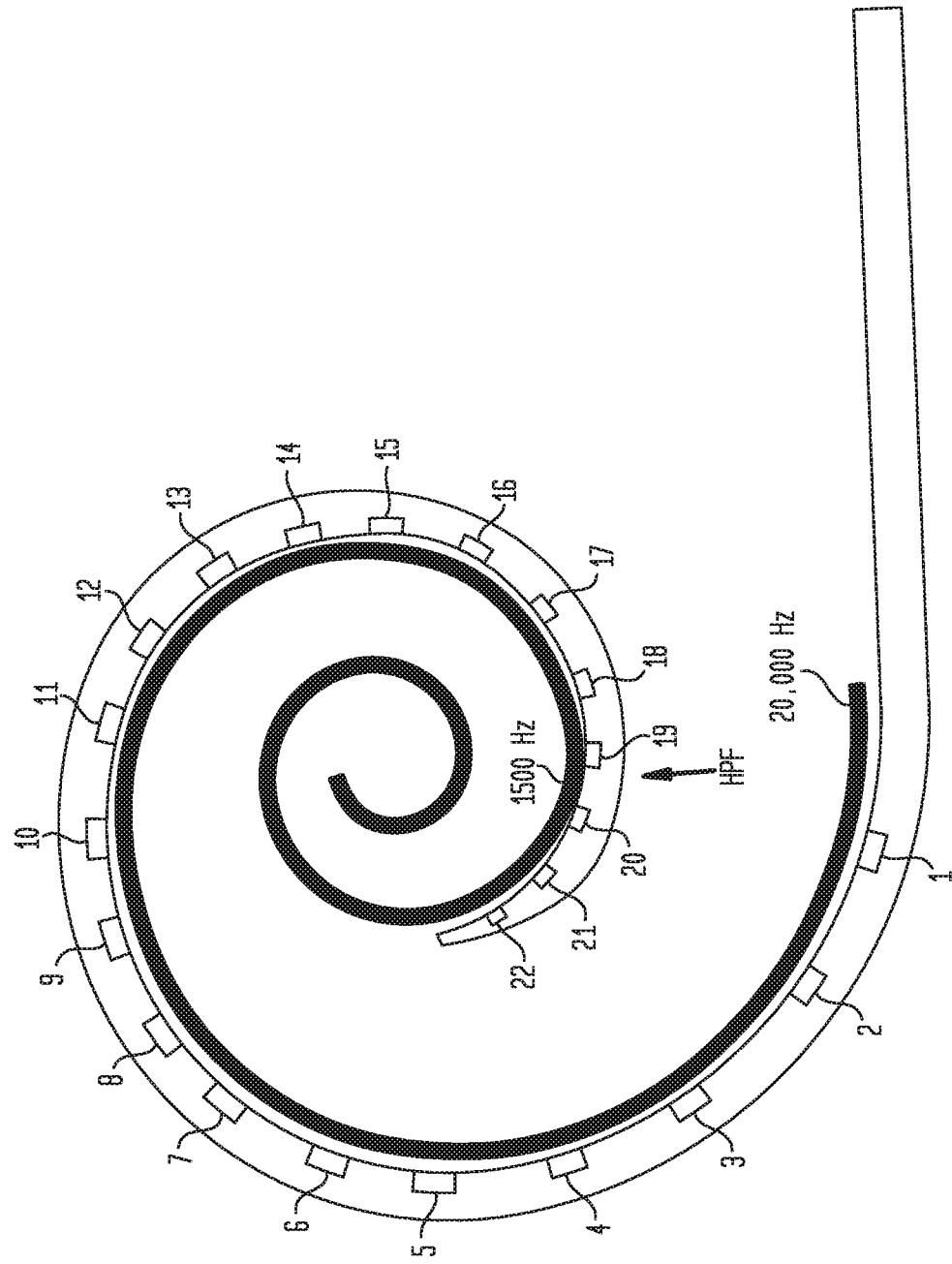
FIG. 5 is a schematic diagram illustrating the positioning of a stimulating assembly in a cochlea of a recipient, in accordance with certain embodiments presented herein.

FIG. 5 is a schematic diagram illustrating the determined angular locations for the electrodes in accordance with the illustrative example. As shown, it is determined that electrodes 20-22 are positioned on the apical side of the HPF (i.e., 370 degree point), while electrodes 1-19 are positioned on the basal side of the HPF. In this example, electrode 19, the nearest basal electrode to the location of the HPF, is set at as the electrical stimulation boundary.

As noted above, after the electrical stimulation boundary is determined, the recipient's trans-impedance matrix is obtained (as described above). Using the trans-impedance matrix, the target apical protection voltage field patterns for the channels in the electrical stimulation zone (i.e., each channel located on the basal side of the electrical stimulation boundary) are determined. For ease of illustration, the determination of only two target apical protection voltage field patterns, namely the pattern associated with a first channel located near to the electrical stimulation boundary and a pattern of a second channel located farther away from the electrical stimulation boundary, are described below. The first channel has electrode 17 as the center electrode, while the second channel has electrode 10 as the center electrode.

Referring to the illustrative first channel at electrode 17, 200 Microampere (μA) of current is delivered via electrode 17 and the resulting voltages on all of the electrodes are determined. As noted above, the voltage at a recording electrode is given as $V=I_{17}Z$, where Z is the impedance between electrode 17 and the recording electrode. FIG. 6A illustrates example expected voltages for each of the electrodes 1-16 and 18-22 upon delivery of the 200 μA of current via electrode 17.

Following determination of the voltages shown in FIG. 6A, the voltages in the protected apical zone (i.e., the electrodes positioned on the apical side of the electrical stimulation boundary) are set to zero. In addition, voltages between the center electrode 17 and the electrical stimulation boundary are scaled/ramped (e.g., in accordance with a step, linear, or other function), resulting in a target apical protection voltage field pattern for electrode 17, given as $V'_{17}$, and shown in FIG. 6B.

Figure 7A:
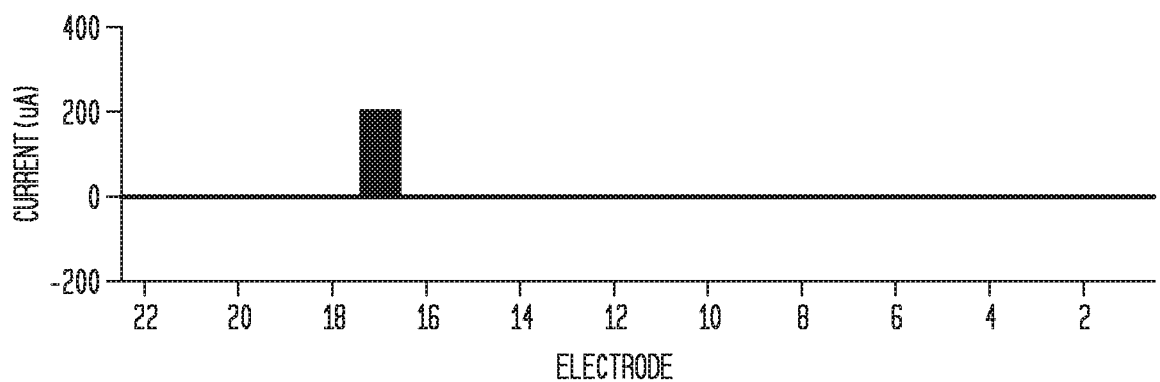
FIG. 7A is a graph illustrating the delivery of current at a selected electrode of a stimulating assembly positioned in a cochlea of a recipient.
Figure 7B:
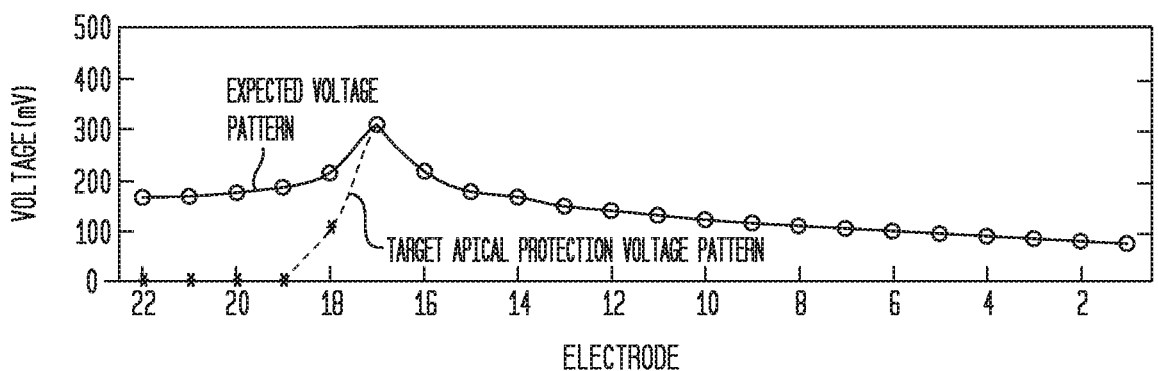
FIG. 7B is a graph illustrating an expected voltage field pattern and a target apical protection current pattern across a stimulating assembly positioned in a cochlea of a recipient, in accordance with certain embodiments presented herein.
Figure 7C:
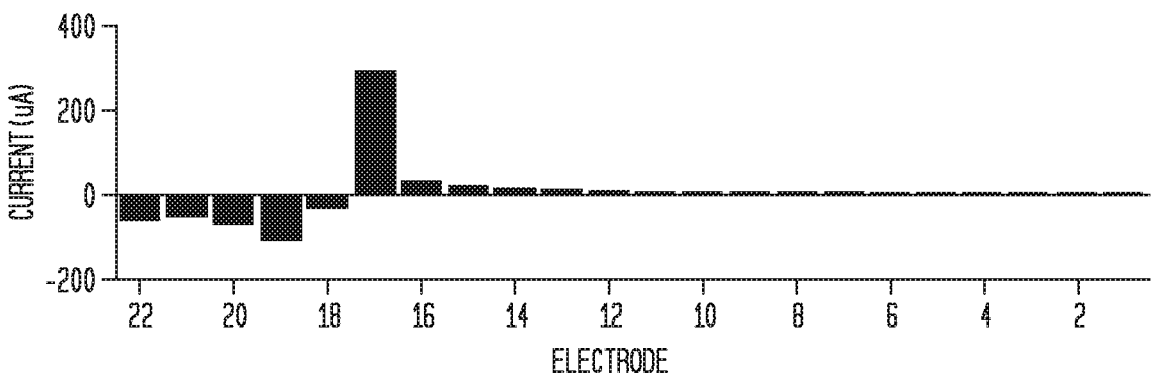
FIG. 7C is a graph illustrating an asymmetric current pattern delivered to the cochlea of the recipient to achieve the target apical protection current pattern of FIG. 7B.

Continuing with reference to the first channel at electrode 17, FIG. 7A is a graph illustrating the delivery of the 200 μA of current via electrode 17. FIG. 7B is a graph illustrating the expected voltage field pattern for electrode 17 (i.e., the voltage field pattern of FIG. 6A) and the target apical protection voltage field pattern (i.e., the voltage field pattern of FIG. 6B). FIG. 7C is a graph illustrating the resulting asymmetric current pattern for delivery via a channel centered at electrode 17 so as to create the protected apical zone (i.e., to ensure that the voltage fields from electrical stimulation signals via the channel centered at electrode 17 are nulled or minimized at locations beyond electrode 19 in order to limit unwanted interactions with any remaining low-frequency hair cells). FIG. 7D is a table listing the current values from FIG. 7C.

Referring to the illustrative second channel at channel 10, 200 Microampere (μA) of current is applied via electrode 10 and the resulting voltages on all of the electrodes are determined. As noted above, the voltage at a recording electrode is given as $V=I_{10}Z$, where Z is the impedance between electrode 10 and the recording electrode. FIG. 8A illustrates an example expected voltage for each of the electrodes 1-9 and 11-22 upon delivery of the 200 μA of current via electrode 10.

Following determination of the voltages shown in FIG. 8A, the voltages in the protected apical zone (i.e., the electrodes positioned on the apical side of the electrical stimulation boundary) are set to zero. In addition, voltages between the center electrode 10 and the electrical stimulation boundary are scaled/ramped, resulting in a target apical protection voltage field pattern for electrode 10, given as $V'_{10}$, and shown in FIG. 8B.

Figure 9A:
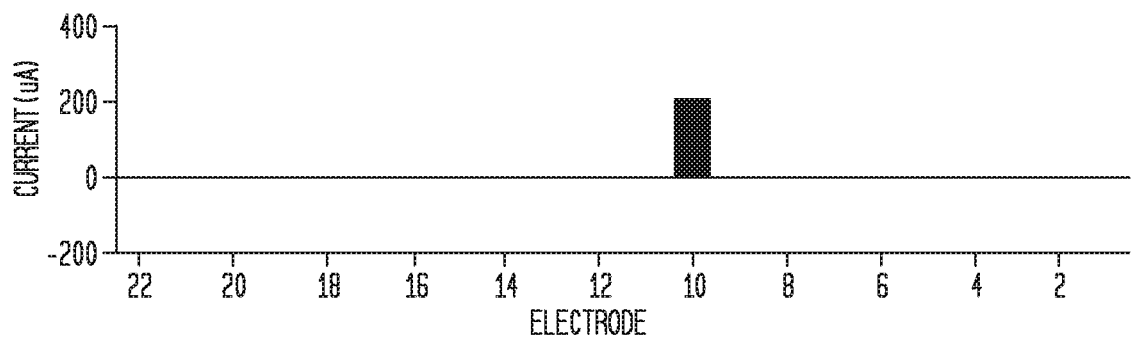
FIG. 9A is a graph illustrating the delivery of current at a selected electrode of a stimulating assembly positioned in a cochlea of a recipient.
Figure 9B:
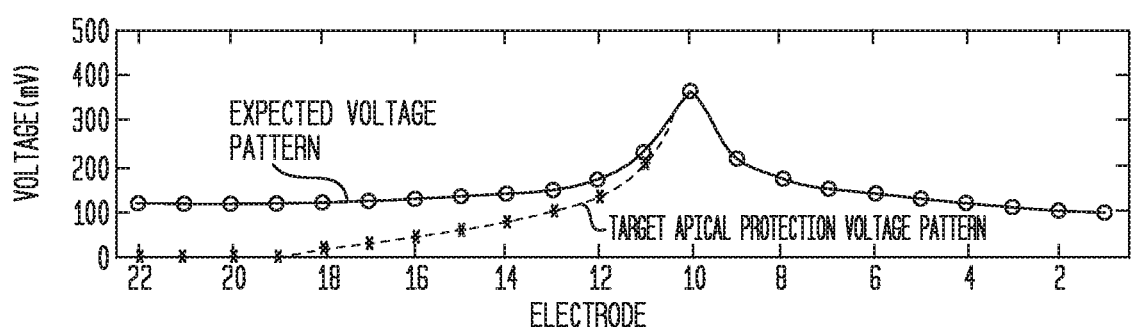
FIG. 9B is a graph illustrating an expected voltage field pattern and a target apical protection current pattern across a stimulating assembly positioned in a cochlea of a recipient, in accordance with certain embodiments presented herein.
Figure 9C:
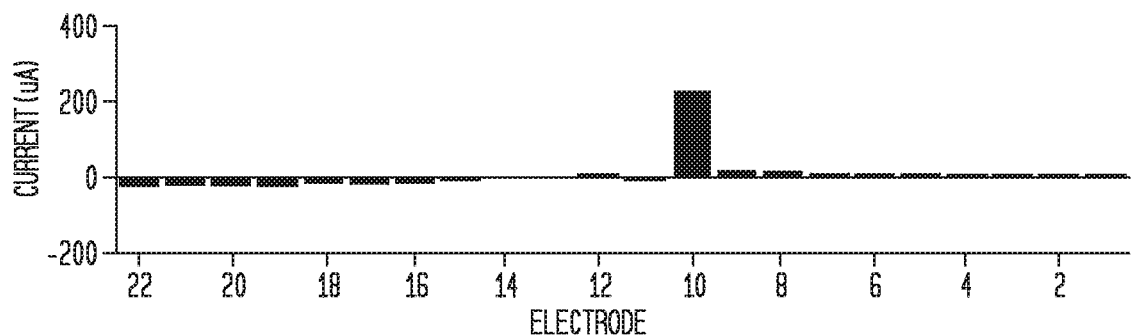
FIG. 9C is a graph illustrating an asymmetric current pattern delivered to the cochlea of the recipient to achieve the target apical protection current pattern of FIG. 7B.

Continuing with reference to the second channel at electrode 10, FIG. 9A is a graph illustrating the delivery of the 200 μA of current via electrode 10. FIG. 9B is a graph illustrating the expected voltage field pattern determine for electrode 10 (i.e., the voltage field pattern of FIG. 8A) and the target apical protection voltage field pattern (i.e., the voltage field pattern of FIG. 8B). FIG. 9C is a graph illustrating the resulting asymmetric current pattern for stimulation via a channel centered at electrode 10 so as to create the protected apical zone (i.e., to ensure that the voltage fields from electrical stimulation signals via the channel centered at electrode 10 are nulled or minimized at locations beyond electrode 19 in order to limit unwanted interactions with any remaining low-frequency hair cells). FIG. 9D is a table listing the current values shown in FIG. 9C.

Figure 10:
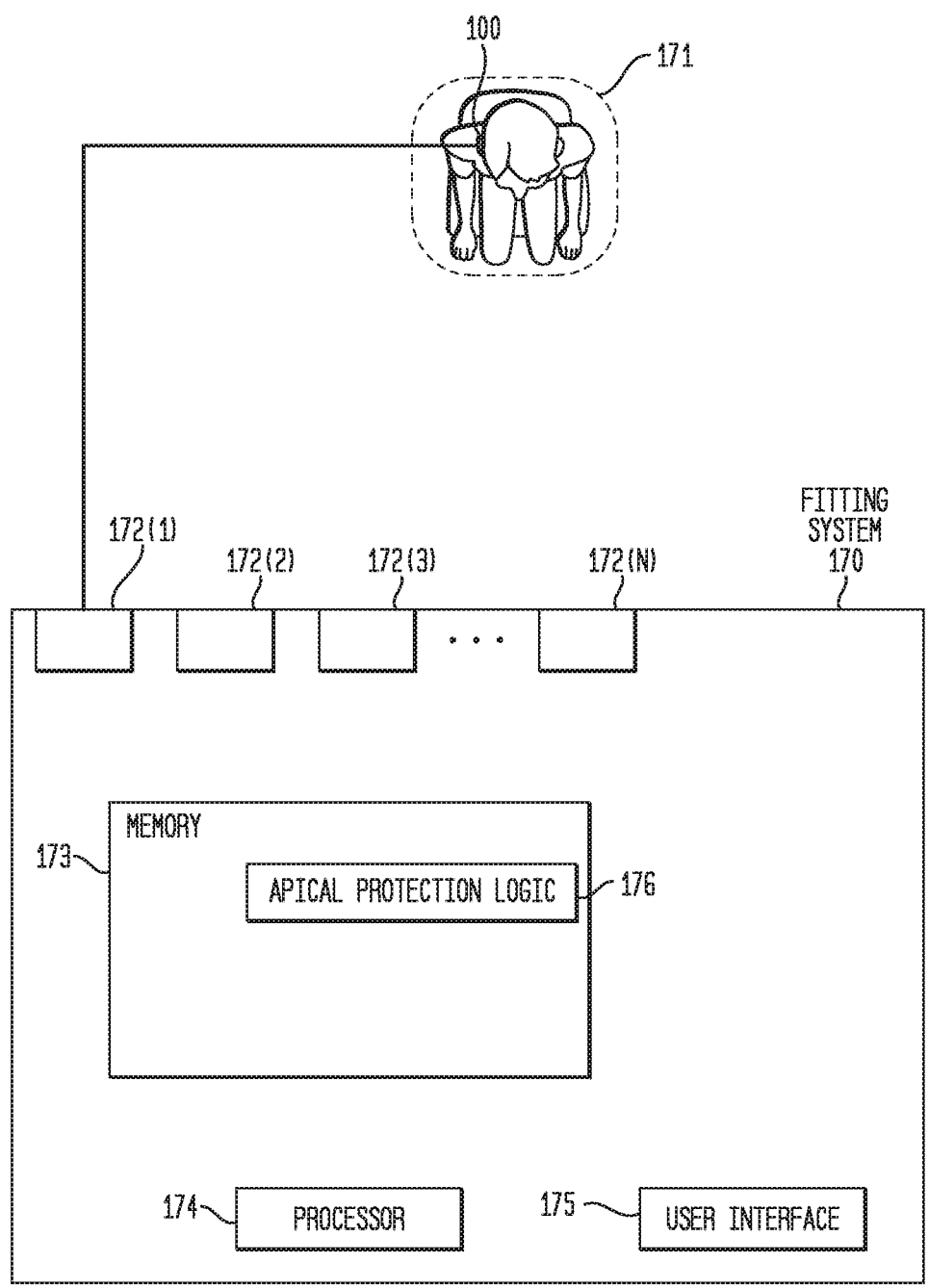
FIG. 10 is a block diagram of a fitting system for implementation of certain techniques presented herein.

As noted above, an auditory prosthesis generally operates in accordance with a number of different operational settings (e.g., settings dictating how an auditory prosthesis operates to convert sound signals into the acoustic and/or electrical stimulation). These operational settings, which are generally determined and set during a fitting process, may include the above described current weights that are configured to create a protected apical zone. FIG. 10 is a block diagram illustrating an example fitting system 170 configured for use in determining the current weights, as well as potentially other operational settings, in accordance with certain embodiments presented herein.

Fitting system 170 is, in general, a computing device that comprises a plurality of interfaces/ports 172(1)-172(N), a memory 173, a processor 174, and a user interface 175. The interfaces 172(1)-172(N) may comprise, for example, any combination of network ports (e.g., Ethernet ports), wireless network interfaces, Universal Serial Bus (USB) ports, Institute of Electrical and Electronics Engineers (IEEE) 1394 interfaces, PS/2 ports, etc. In the example of FIG. 10, interface 172(1) is connected to electro-acoustic hearing prosthesis 100 having components implanted in a recipient 171. Interface 172(1) may be directly connected to the electro-acoustic hearing prosthesis 100 or connected to an external device that is communication with the electro-acoustic hearing prosthesis 100. Interface 172(1) may be configured to communicate with electro-acoustic hearing prosthesis 100 via a wired or wireless connection (e.g., to provide generated relative asymmetric current weights for the stimulation channels to the electro-acoustic hearing prosthesis 100 for generation of current signals, in real-time, for delivery to the recipient).

The user interface 175 includes one or more output devices, such as a liquid crystal display (LCD) and a speaker, for presentation of visual or audible information to a clinician, audiologist, or other user. The user interface 175 may also comprise one or more input devices that include, for example, a keypad, keyboard, mouse, touchscreen, etc.

The memory 173 comprises apical protection logic 176 that may be executed to generate or update current weights for use in the recipient's electro-acoustic hearing prosthesis 100 (e.g., execute method 160 described above). It would be appreciated that memory 173 may include other logic elements that, for ease of illustration, have been omitted from FIG. 10.

Memory 173 may comprise read only memory (ROM), random access memory (RAM), magnetic disk storage media devices, optical storage media devices, flash memory devices, electrical, optical, or other physical/tangible memory storage devices. The processor 174 is, for example, a microprocessor or microcontroller that executes instructions for the apical protection logic 176. Thus, in general, the memory 173 may comprise one or more tangible (non-transitory) computer readable storage media (e.g., a memory device) encoded with software comprising computer executable instructions and when the software is executed (by the processor 174) it is operable to perform operations described herein.

It is to be appreciated that the arrangement for fitting system 170 shown in FIG. 10 is illustrative and that a fitting system 170 in accordance with embodiments presented herein may include any combination of hardware, software, and firmware configured to perform the functions described herein. For example, the fitting system 170 may be a personal computer, handheld device (e.g., a tablet computer), a mobile device (e.g., a mobile phone), and/or any other electronic device.

FIG. 11 is a flowchart of a method 180 in accordance with embodiments presented herein. For ease of illustration, method 180 will be described with reference to electro-acoustic hearing prosthesis 100 of FIGS. 1A, 1B, and 2.

Method 180 begins at 182 where an auditory prosthesis, which comprises a stimulating assembly implanted in a cochlea of a recipient, obtains sounds. The stimulating assembly comprises a plurality of longitudinally spaced electrodes. At 184, the auditory prosthesis converts the sounds into a first set of current signals for delivery to the cochlea of the recipient. At 186, the auditory prosthesis delivers the current signals to the cochlea via a first set of electrodes, wherein the current signals are asymmetrically weighted to evoke perception of one or more frequencies of the sound signals and to substantially null, at locations apical to a predetermined location in the cochlea. In these examples, the auditory prosthesis may be, for example, a cochlear implant, an electro-acoustic hearing prosthesis, tinnitus stimulator, etc. The sounds may be obtained by receiving acoustic sound signals via one or more sound input device, by retrieving sound files from a memory of the auditory prosthesis, etc.

As noted, embodiments of the present invention have been described herein with reference to one specific type of auditory prosthesis, namely an electro-acoustic hearing prosthesis comprising a cochlear implant portion and a hearing aid portion. However, it is to be appreciated that the techniques presented herein may be used with other types of hearing prostheses, such as bi-modal hearing prostheses, electro-acoustic hearing prosthesis comprising other types of output devices (e.g., auditory brainstem stimulators, direct acoustic stimulators, bone conduction devices, etc.), tinnitus stimulators, etc. The techniques presented herein may also be used with different length intra-cochlear stimulating assemblies, intra-cochlear stimulating assemblies having different numbers of electrodes, etc.

It is to be appreciated that the embodiments presented herein are not mutually exclusive.

The invention described and claimed herein is not to be limited in scope by the specific preferred embodiments herein disclosed, since these embodiments are intended as illustrations, and not limitations, of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

What is claimed is:

1. A method, comprising:
determining an electrical stimulation boundary within a cochlea of a recipient of an auditory prosthesis comprising an intra-cochlear stimulating assembly, the recipient having residual hearing at an apical side of the electrical stimulation boundary, wherein the intra-cochlear stimulating assembly comprises a plurality of longitudinally spaced electrodes forming a plurality of multipolar stimulation channels; and
determining current weights for at least one of the plurality of multipolar stimulation channels at a basal side of the electrical stimulation boundary,
wherein the current weights for the at least one of the plurality of multipolar stimulation channels at the basal side of the electrical stimulation boundary are set for delivery of current signals to the cochlea via the at least one of the plurality of multipolar stimulation channels to evoke perception of one or more frequencies of a sound obtained at the auditory prosthesis while creating nulled voltage fields across the apical side of the electrical stimulation boundary and to create voltages at the plurality of longitudinally spaced electrodes that include a peak voltage and that asymmetrically decrease from the peak voltage.

2. The method of claim 1, wherein when the current signals are delivered to regions of the cochlea at the basal side of the electrical stimulation boundary, the nulled voltage fields across the apical side of the electrical stimulation boundary have amplitudes that are below a predetermined threshold.

3. The method of claim 1, wherein the at least one of the plurality of multipolar stimulation channels includes a central electrode associated with one of the current weights and one or more secondary electrodes of the plurality of longitudinally spaced electrodes each associated with another one of the current weights, and wherein the central electrode has the peak voltage.

4. The method of claim 3, wherein values of the current weights associated with the one or more secondary electrodes are a function of a distance between the one or more secondary electrodes and the electrical stimulation boundary.

5. The method of claim 1, wherein determining the electrical stimulation boundary comprises:
setting the electrical stimulation boundary at a specific electrode of the plurality of longitudinally spaced electrodes of the intra-cochlear stimulating assembly beyond which, in an apical direction, a voltage field resulting from the delivery of the current signals is controlled in order to limit electro-acoustic interactions on the apical side of the electrical stimulation boundary.

6. The method of claim 5, wherein setting the electrical stimulation boundary at the specific electrode of the intra-cochlear stimulating assembly comprises:
determining frequency areas of the cochlea having acoustic thresholds that are less than a predetermined threshold hearing level;
determining a location of a highest protected frequency as a highest frequency area of the cochlea having acoustic thresholds that are less than the predetermined threshold hearing level;
determining an angular location of the highest protected frequency;
determining angular locations of the plurality of longitudinally spaced electrodes; and
setting the electrical stimulation boundary as the specific electrode of the plurality of longitudinally spaced electrodes based on the specific electrode having a selected angular location that is on the basal side of the highest protected frequency.

7. The method of claim 6, wherein setting the electrical stimulation boundary as the specific electrode based on the specific electrode having the selected angular location that is on the basal side of the highest protected frequency comprises:
   setting the electrical stimulation boundary at the specific electrode based on the selected angular location of the specific electrode being closest to the angular location of the highest protected frequency and on the basal side of the highest protected frequency.

8. The method of claim 6, wherein setting the electrical stimulation boundary as the specific electrode based on the specific electrode having the selected angular location that is on the basal side of the highest protected frequency comprises:
   setting the electrical stimulation boundary at the specific electrode based on the selected angular location of the specific electrode being spaced from the angular location of the highest protected frequency by one or more other electrodes of the plurality of longitudinally spaced electrodes.

9. The method of claim 1, wherein determining the current weights for the at least one of the plurality of multipolar stimulation channels comprises:
   determining at least one target apical protection voltage field pattern for at least one multipolar stimulation channel of the plurality of multipolar stimulation channels centered at the basal side of the electrical stimulation boundary, wherein the at least one target apical protection voltage field pattern is substantially nulled across the apical side of the electrical stimulation boundary; and
   determining the current weights set for delivery of the current signals to the cochlea via the at least one multipolar stimulation channel to evoke the perception of the one or more frequencies of the sound obtained at the auditory prosthesis while creating the at least one target apical protection voltage field pattern.

10. The method of claim 9, wherein determining the at least one target apical protection voltage field pattern for the at least one multipolar stimulation channel centered at the basal side of the electrical stimulation boundary comprises:
    obtaining a trans-impedance matrix for the plurality of longitudinally spaced electrodes;
    determining, based on the trans-impedance matrix, an expected voltage field pattern for the at least one multipolar stimulation channel; and
    converting the expected voltage field pattern to the at least one target apical protection voltage field pattern by setting voltages for a set of electrodes of the plurality of longitudinally spaced electrodes located at, and on the apical side of, the electrical stimulation boundary to a value of zero.

11. The method of claim 10, wherein converting the expected voltage field pattern to the at least one target apical protection voltage field pattern further comprises:
    adjusting voltages at one or more electrodes of the plurality of longitudinally spaced electrodes between the electrical stimulation boundary and a central electrode of the at least one multipolar stimulation channel.

12. The method of claim 1, further comprising:
    providing the current weights for the at least one of the plurality of multipolar stimulation channels to the auditory prosthesis for use in delivering the current signals to the cochlea of the recipient.

13. A method, comprising:
    obtaining sounds at a hearing device comprising a stimulating assembly implanted in a cochlea of a recipient having residual hearing at locations apical to a predetermined location in the cochlea, wherein the stimulating assembly comprises a plurality of longitudinally spaced electrodes;
    converting the sounds into a first set of current signals for delivery to the cochlea of the recipient; and
    delivering the first set of current signals to the cochlea via a first set of electrodes of the plurality of longitudinally spaced electrodes,
    wherein the first set of current signals are asymmetrically weighted with asymmetric current weights to evoke perception of one or more frequencies of the sounds, to substantially null, at the locations apical to the predetermined location in the cochlea, a voltage field, to define a central electrode of the first set of electrodes having a peak voltage, and to create voltages that asymmetrically decrease from the central electrode resulting from delivery of the first set of current signals to the cochlea.

14. The method of claim 13, wherein the first set of electrodes includes a plurality of secondary electrodes each associated with one of the asymmetric current weights.

15. The method of claim 14, wherein values of the asymmetric current weights associated with the plurality of secondary electrodes are a function of a distance between the plurality of secondary electrodes and the predetermined location in the cochlea.

16. The method of claim 13, wherein the predetermined location in the cochlea is a selected one of the plurality of longitudinally spaced electrodes.

17. The method of claim 13, wherein obtaining the sounds, comprises:
    receiving acoustic sound signals via one or more sound input devices.

18. The method of claim 13, wherein obtaining the sounds, comprises:
    obtaining sound files from a memory of the hearing device.

19. A method, comprising:
    determining an electrical stimulation boundary within a cochlea of a recipient of a medical device comprising an intra-cochlear stimulating assembly, the recipient having residual hearing at an apical side of the electrical stimulation boundary, wherein the intra-cochlear stimulating assembly comprises a plurality of longitudinally spaced electrodes forming a plurality of multipolar stimulation channels; and
    determining asymmetric current weights for at least one of the plurality of multipolar stimulation channels at a basal side of the electrical stimulation boundary,
    wherein the asymmetric current weights are set for delivery of current signals to the cochlea via the at least one of the plurality of multipolar stimulation channels to evoke perception of one or more frequencies of a sound obtained at the medical device, to control a spread of current beyond, in an apical direction, the electrical stimulation boundary in the cochlea, to define a central electrode of the plurality of longitudinally spaced electrodes at which a peak voltage is present, and to create a voltage field that decreases from the central electrode in a basal direction and in the apical direction, the decrease of the voltage field from the central electrode in the basal direction and the decrease of the voltage field from the central electrode in the apical direction being asymmetrical about the central electrode.

20. The method of claim 19, wherein the asymmetric current weights are set such that, when the current signals are delivered to the cochlea via the at least one of the plurality of multipolar stimulation channels, a region of the cochlea at the apical side of the electrical stimulation boundary will be exposed to average voltage fields that are below a predetermined threshold.

21. The method of claim 19, wherein the at least one of the plurality of multipolar stimulation channels includes a plurality of secondary electrodes each associated with one of the asymmetric current weights.

22. The method of claim 19, wherein determining the electrical stimulation boundary comprises:
  setting the electrical stimulation boundary at a specific electrode of the plurality of longitudinally spaced electrodes of the intra-cochlear stimulating assembly beyond which, in the apical direction, the voltage field resulting from the delivery of the current signals is controlled in order to limit electro-acoustic interactions on the apical side of the electrical stimulation boundary.

23. The method of claim 22, wherein setting the electrical stimulation boundary at the specific electrode of the intra-cochlear stimulating assembly comprises:
  determining frequency areas of the cochlea having acoustic thresholds that are less than a predetermined threshold hearing level;
  determining a location of a highest protected frequency as a highest frequency area of the cochlea having acoustic thresholds that are less than the predetermined threshold hearing level;
  determining an angular location of the highest protected frequency;
  determining angular locations of the plurality of longitudinally spaced electrodes; and
  setting the electrical stimulation boundary as the specific electrode of the plurality of longitudinally spaced electrodes based on the specific electrode having a selected angular location that is on the basal side of the highest protected frequency.

24. One or more non-transitory computer readable storage media encoded with instructions that, when executed by a processor, cause the processor to:
  determine a predetermined location within a cochlea of a recipient of a medical device comprising an intra-cochlear stimulating assembly, the recipient having residual hearing at locations apical to the predetermined location, wherein the intra-cochlear stimulating assembly comprises a plurality of longitudinally spaced electrodes; and
  determine asymmetric current weights for a first set of the plurality of longitudinally spaced electrodes,
  wherein the asymmetric current weights are configured for use in generating current signals for delivery to the cochlea via the first set of the plurality of longitudinally spaced electrodes to evoke perception of one or more frequencies of a sound obtained at the medical device, to substantially null, at the locations apical to the predetermined location in the cochlea, a voltage field resulting from the delivery of the current signals to the cochlea, to define a central electrode of the first set of the plurality of longitudinally spaced electrodes associated with a peak voltage, and to create voltages, at the central electrode and secondary electrodes of the plurality of longitudinally spaced electrodes immediately adjacent to the central electrode, that are asymmetrical about the central electrode.

25. The one or more non-transitory computer readable storage media of claim 24, wherein the asymmetric current weights are configured such that, when the current signals are delivered via the first set of the plurality of longitudinally spaced electrodes, a region of the cochlea at an apical side of the predetermined location in the cochlea will be exposed to average voltage fields that are below a predetermined threshold.

26. The one or more non-transitory computer readable storage media of claim 24, wherein the central electrode and the secondary electrodes are each associated with one of the asymmetric current weights.

27. The one or more non-transitory computer readable storage media of claim 26, wherein values of each of the asymmetric current weights associated with the secondary electrodes are a function of a distance between the secondary electrodes and the predetermined location in the cochlea.

28. The one or more non-transitory computer readable storage media of claim 24, further comprising instructions that, when executed by the processor, cause the processor to:
  set the predetermined location within the cochlea.

29. The one or more non-transitory computer readable storage media of claim 28, wherein the instructions that cause the processor to set the predetermined location within the cochlea cause the processor to:
  set the predetermined location within the cochlea at a specific electrode of the plurality of longitudinally spaced electrodes of the intra-cochlear stimulating assembly beyond which, in an apical direction, the voltage field resulting from the delivery of the current signals is controlled in order to limit electro-acoustic interactions.

30. The one or more non-transitory computer readable storage media of claim 29, wherein the instructions that cause the processor to set the predetermined location at the specific electrode of the intra-cochlear stimulating assembly cause the processor to:
  determine frequency areas of the cochlea having acoustic thresholds that are less than a predetermined threshold hearing level;
  determine a location of a highest protected frequency as a highest frequency area of the cochlea having acoustic thresholds that are less than the predetermined threshold hearing level;
  determine an angular location of the highest protected frequency;
  determine angular locations of the plurality of longitudinally spaced electrodes; and
  set an electrical stimulation boundary as the specific electrode of the plurality of longitudinally spaced electrodes based on the specific electrode having a selected angular location that is on a basal side of the highest protected frequency.

31. The one or more non-transitory computer readable storage media of claim 24, wherein a first difference between the peak voltage and a first voltage of a most apical electrode of the plurality of longitudinally spaced electrodes is different from a second difference between the peak voltage and a second voltage of a most basal electrode of the plurality of longitudinally spaced electrodes.

32. The one or more non-transitory computer readable storage media of claim 31, wherein the second voltage of the most basal electrode is positive.

33. The one or more non-transitory computer readable storage media of claim 31, wherein the first difference is greater than the second difference.

34. The method of claim 13, wherein the first set of current signals create a first voltage at a first electrode immediately adjacent to the central electrode in an apical direction and a second voltage at a second electrode immediately adjacent to the central electrode in a basal direction, and wherein a first difference between the peak voltage of the central electrode and the first voltage of the first electrode is different from a second difference between the peak voltage of the central electrode and the second voltage of the second electrode.

35. The method of claim 34, wherein the first voltage of the first electrode, the second voltage of the second electrode, or both are positive.

36. The method of claim 35, wherein the second voltage is greater than the first voltage.

* * * * *